United States Patent
Babkes et al.

(10) Patent No.: US 9,956,105 B2
(45) Date of Patent: May 1, 2018

(54) UPPER STOMACH GASTRIC IMPLANTS

(71) Applicant: Apollo Endosurgery, Inc., Austin, TX (US)

(72) Inventors: Mitchell H. Babkes, Santa Clarita, CA (US); Zachary P. Dominguez, Santa Barbara, CA (US)

(73) Assignee: Apollo Endosurgery US, Inc., Austin, TX (US)

( * ) Notice: Subject to any disclaimer, the term of this patent is extended or adjusted under 35 U.S.C. 154(b) by 160 days.

(21) Appl. No.: 14/883,565

(22) Filed: Oct. 14, 2015

(65) Prior Publication Data
US 2016/0030219 A1    Feb. 4, 2016

Related U.S. Application Data

(62) Division of application No. 13/275,166, filed on Oct. 17, 2011, now Pat. No. 9,198,790.

(60) Provisional application No. 61/485,009, filed on May 11, 2011, provisional application No. 61/394,592, filed on Oct. 19, 2010.

(51) Int. Cl.
*A61M 29/00* (2006.01)
*A61F 5/00* (2006.01)

(52) U.S. Cl.
CPC .......... *A61F 5/0036* (2013.01); *A61F 5/0003* (2013.01); *A61F 5/003* (2013.01); *A61F 5/0013* (2013.01); *A61F 5/0033* (2013.01); *A61F 5/0076* (2013.01); *A61F 5/0086* (2013.01); *A61F 5/0079* (2013.01); *A61F 5/0089* (2013.01); *Y10T 24/4453* (2015.01); *Y10T 24/44342* (2015.01); *Y10T 24/44564* (2015.01)

(58) Field of Classification Search
CPC ...... A61F 5/0003; A61F 5/0013; A61F 5/003; A61F 5/0033; A61F 5/0076; A61F 5/0086; A61F 5/0036; A61F 5/0089; Y10T 24/44564; Y10T 24/44342; Y10T 24/4453
See application file for complete search history.

(56) References Cited

U.S. PATENT DOCUMENTS

| | | | | |
|---|---|---|---|---|
| 2005/0228504 A1* | 10/2005 | Demarais | ......... | A61B 17/12099 623/23.65 |
| 2007/0083224 A1* | 4/2007 | Hively | ......... | A61F 5/0036 606/192 |
| 2009/0171382 A1* | 7/2009 | Dillon | ......... | A61F 5/0036 606/192 |

* cited by examiner

*Primary Examiner* — Richard Louis
(74) *Attorney, Agent, or Firm* — Donald K. Jones

(57) ABSTRACT

A variety of passive intragastric implant devices for obesity treatment are disclosed. Such passive devices do not autonomously change shape, but instead react within the stomach to induce satiety. The devices may provide slowed entry into the stomach, thus reducing the intake capacity. Additionally, the devices may contact areas within the stomach, such as the cardia surrounding the esophageal sphincter, to stimulate satiety-inducing nerves. Some devices combine two or more of these satiety-inducing features. Methods of implant are disclosed including compressing the devices within a delivery tube and transorally advancing the devices through the esophagus to be deployed within the stomach. Removal of the devices occurs in the reverse. The implants are formed of materials that permit the implant to be compressed into a substantially linear transoral delivery configuration and that will resist degradation over a period of at least six months within the stomach.

15 Claims, 9 Drawing Sheets

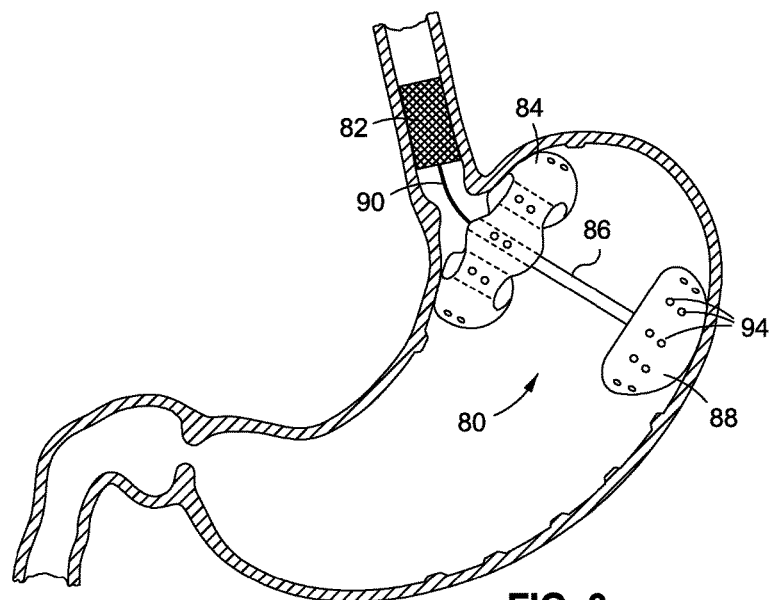
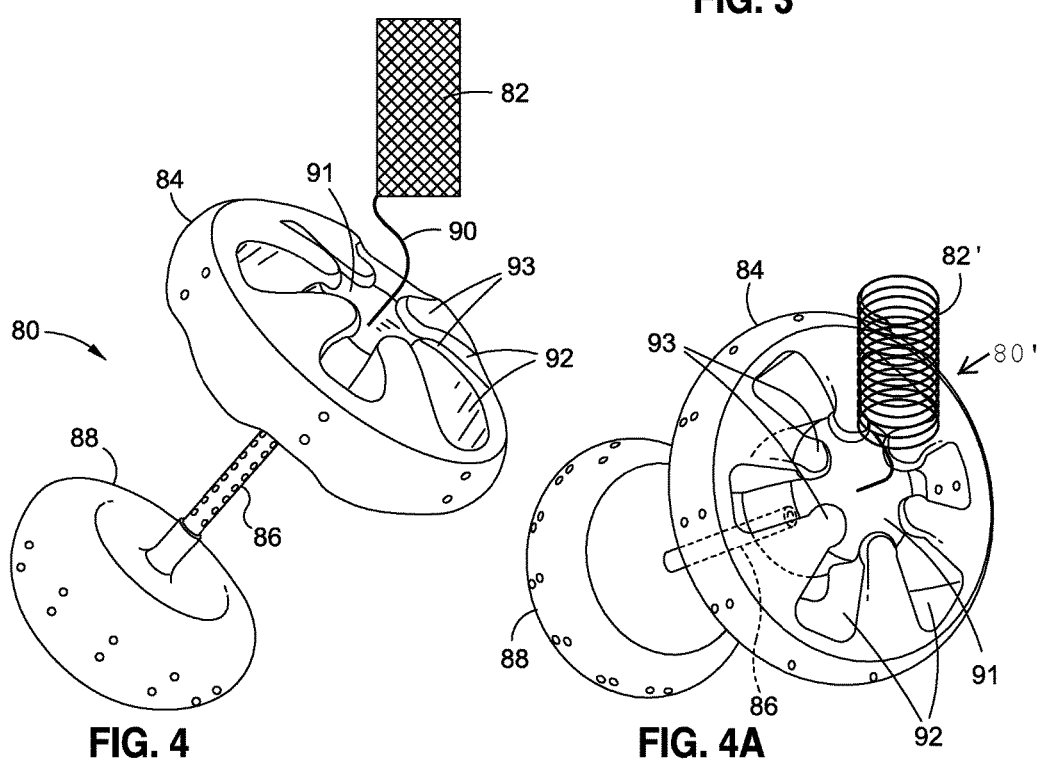
FIG. 3
FIG. 4
FIG. 4A

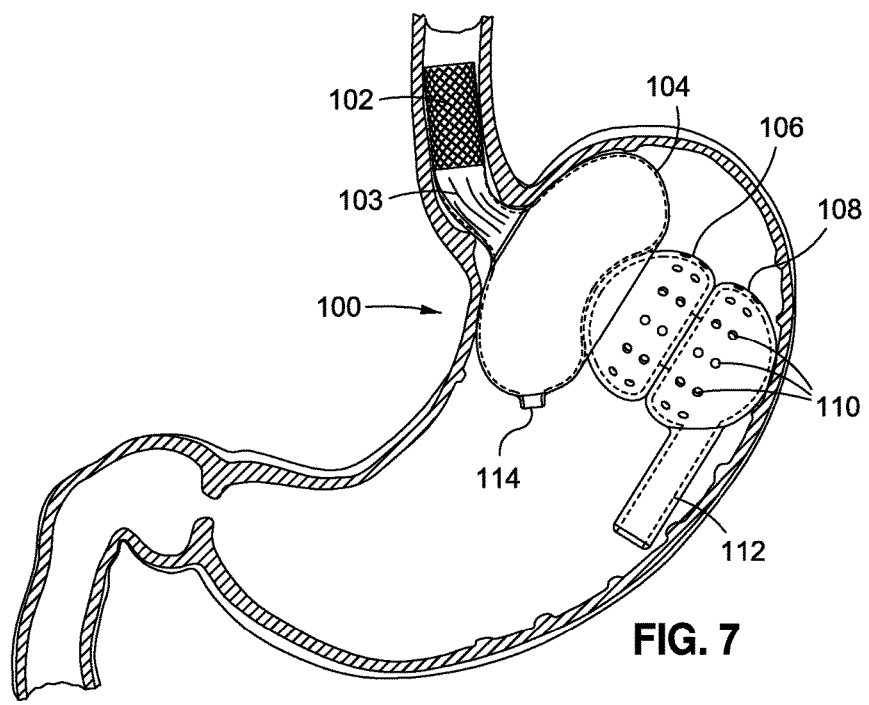
FIG. 7
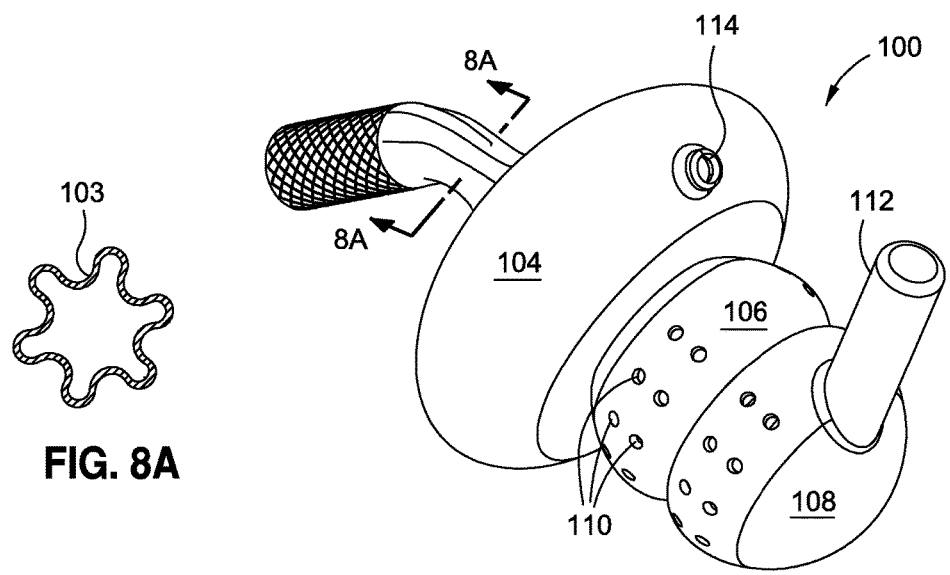
FIG. 8A
FIG. 8

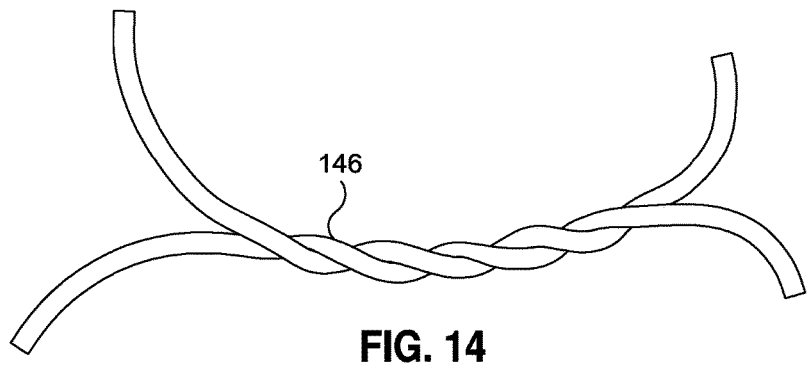
FIG. 14
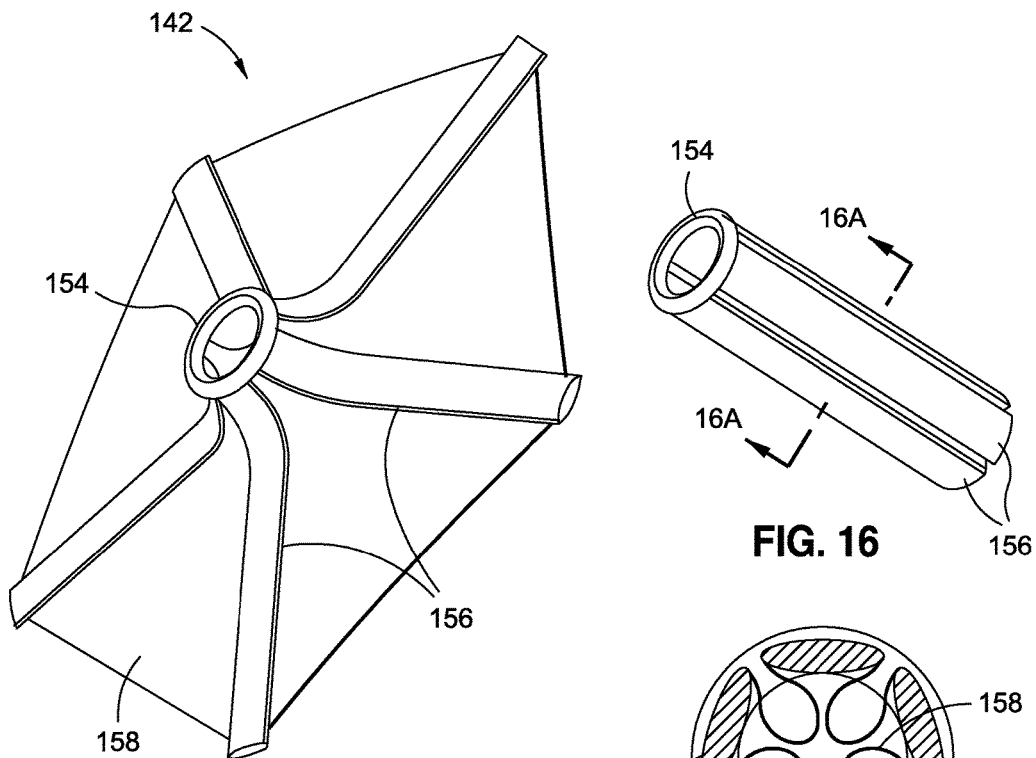
FIG. 15
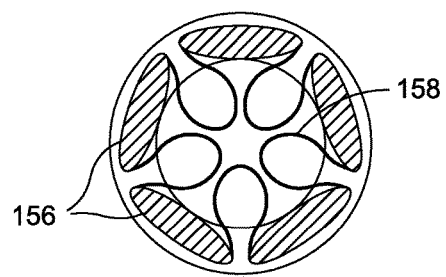
FIG. 16
FIG. 16A

UPPER STOMACH GASTRIC IMPLANTS

CROSS-REFERENCE TO RELATED APPLICATIONS

The present application is a divisional of U.S. Ser. No. 13/275,166, filed Oct. 17, 2011, which claims priority under 35 U.S.C. § 119 to U.S. Provisional Application No. 61/485,009, filed May 11, 2011, and to 61/394,592, filed Oct. 19, 2010, the disclosures of which are incorporated by reference herein.

FIELD OF THE INVENTION

The present invention is directed to intragastric devices used for the treatment of obesity, and in particular to devices and systems for placement in and adjacent to the stomach cavity.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States was estimated to be about 400,000 in 2010.

Examples of surgical methods and devices used to treat obesity include the LAP-BAND® (Allergan Medical of Irvine, Calif.) gastric band and the LAP-BAND AP® (Allergan). However, surgery might not be an option for every obese individual; for certain patients, non-surgical therapies or minimal-surgery options are more effective or appropriate.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These devices are designed to provide therapy for moderately obese individuals who need to shed pounds in preparation for surgery, or as part of a dietary or behavioral modification program. These balloons are typically cylindrical or pear-shaped, generally range in size from 200-500 ml or more, are made of an elastomer such as silicone, polyurethane, or latex, and are filled with air, an inert gas, water, or saline.

One such inflatable intragastric balloon is described in U.S. Pat. No. 5,084,061 and is commercially available as the BioEnterics Intragastric Balloon System ("BIB System," sold under the trademark ORBERA). The BIB System comprises a silicone elastomer intragastric balloon that is inserted into the stomach and filled with fluid. Conventionally, the balloons are placed in the stomach in an empty or deflated state and thereafter filled (fully or partially) with a suitable fluid. The balloon occupies space in the stomach, thereby leaving less room available for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Placement of such balloons is temporary, and such balloons are typically removed after about six months. Removing the balloon requires deflation by puncturing with a gastroscopic instrument, and either aspirating the contents of the balloon and removing it, or allowing the fluid to pass into the patient's stomach. Clinical results with these devices show that for many obese patients, the intragastric balloons significantly help to control appetite and accomplish weight loss.

Some attempted solutions for weight loss by placing devices in the stomach result in unintended consequences. For instance, some devices tend to cause food and liquid to back up in the stomach, leading to symptoms of gastroesophageal reflux disease (GERD), a condition in which the stomach contents (food or liquid) leak backwards from the stomach into the esophagus. Also, the stomach acclimates to some gastric implant devices, leading to an expansion of stomach volume and consequent reduction in the efficacy of the device.

Therefore, despite many advances in the design of intragastric obesity treatment devices, there remains a need for improved devices that can be implanted for longer periods than before or otherwise address certain drawbacks of intragastric balloons and other such implants.

SUMMARY OF THE INVENTION

The present invention addresses the above-described problems by providing passive intragastric apparatuses and methods for inducing satiety and therefore treating obesity. Such passive devices do not autonomously change shape, but instead react within the stomach to induce satiety. The devices may take up volume within the stomach, thus reducing the intake capacity. Additionally, the devices may contact areas within the stomach, such as the cardia surrounding the esophageal sphincter, to stimulate satiety-inducing nerves. Also, a number of devices slow gastric filling by impeding flow through the esophageal sphincter. A number of devices combine two or more of these satiety-inducing features. Methods of implant are disclosed including compressing the devices within a delivery tube and transorally advancing the devices through the esophagus to be deployed within the stomach. Removal of the devices occurs in the reverse.

Each of the implants described herein is formed of materials that permit it to be compressed into a substantially linear transoral delivery configuration and that will resist degradation over a period of at least six months within the stomach.

In accordance with a first preferred embodiment, a passive intragastric obesity treatment implant comprises an esophageal stent sized to anchor within the esophagus just above the esophageal sphincter. A shallow conical ring is sized to contact the interior stomach walls adjacent to the esophageal sphincter with a central through hole centered at the esophageal sphincter, and a thin, flexible tether connects the esophageal stent to the conical ring. A plurality of thin anchor legs extend from a distal rim of the conical ring, the legs made of a resilient material. Finally, a shallow cup member attaches to the anchor legs opposite from the conical ring and is sized to create large spaces between the conical ring and the cup member, the anchor legs having a sufficient length such that the cup member contacts an interior stomach wall opposite the esophageal sphincter. There are desirably four anchor legs, and the tether is preferably relatively flexible while the anchor legs are relatively stiffer to transmit compressive forces from the cup member to the conical ring.

Another aspect of the present application is a passive intragastric obesity treatment implant that comprises an esophageal stent sized to anchor within the esophagus just above the esophageal sphincter. A cardia-stimulating pillow having perforations and a central opening align with the esophageal sphincter to permit food to pass therethrough. A flexible tether secures the cardia-stimulating pillow to the esophageal stent. A balloon-like pillow smaller than the cardia-stimulating pillow and having perforations therein connects to the cardia-stimulating pillow via a thin relatively stiff tube, the tube having a length sufficient to maintain contact of the cardia-stimulating pillow against the cardia and the balloon-like pillow against the stomach wall opposite the esophageal sphincter. The cardia-stimulating pillow preferably comprises a substantially disk-shaped member having large spoke-like through holes for passage of food. The cardia-stimulating pillow may further include a central hub connected to both the tube and tether. The esophageal stent may be a tubular stent or a coil of elastic material, such as Nitinol. In one embodiment, the cardia-stimulating pillow and the balloon-like pillow are molded with relatively thick walls to maintain their as-molded shape without inflation, and each includes holes to allow stomach juices to freely flow in and out.

In accordance with another embodiment, a passive intragastric obesity treatment implant includes an esophageal stent sized to anchor within the esophagus just above the esophageal sphincter. An enlarged cardia-stimulating pillow tethers to the esophageal stent to abut the esophageal opening and is open to the esophagus, the pillow including an artificial stoma opening to the stomach cavity. A plurality of balloon-like pillows having perforations stack against the cardia-stimulating pillow so as to reach the interior stomach wall opposite the esophageal sphincter and thus maintain contact of the cardia-stimulating pillow against the cardia. The artificial stoma may be an aperture in a flexible diaphragm such that the artificial stoma has a variable diameter. The implant may further comprise an anti-rotation leg attached to an outer one of the balloon-like pillows. Preferably, wherein there are two balloon-like pillows each having a substantially hemispherical shape and arranged so that their equatorial planes abut. Desirably, the balloon-like pillows are molded with relatively thick walls to maintain their as-molded shape without inflation, and each includes holes to allow stomach juices to freely flow in and out. The cardia-stimulating pillow may be tethered to the esophageal stent by a collapsible tubular connector between the esophageal stent and the cardia-stimulating pillow, the tubular connector permitting food to flow therethrough from the esophagus into the interior of the pillow.

A further passive intragastric obesity treatment implant of the present application comprises an esophageal mounting stent sized to anchor within the esophagus just above the esophageal sphincter, the stent having a configuration that allows it to change its outer diameter while maintaining an inner diameter aperture substantially constant. An enlarged cardia-stimulating umbrella tethered to the esophageal stent has a contracted columnar shape for delivery and an expanded splayed out shape that abuts against the cardia surrounding the esophageal sphincter. The esophageal mounting stent may have an accordion-like spiral structure include a plurality of triangular membranes that are each bordered on two sides by an upper strut and a lower strut, with an outer edge being free. The cardia-stimulating umbrella preferably comprises a plurality of strips splayed outward from a central hub, and flexible webbing extending between the strips, wherein the strips are relatively stiff in comparison to the webbing. The central hub is preferably an open ring for food to pass therethrough.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIG. 3 shows another obesity treatment device having a cardia-stimulating pillow, and FIG. 4 is a perspective view thereof;

FIGS. 4A and 6 are perspective views thereof;

FIG. 7 shows an obesity treatment device having a cardia-stimulating pillow supported by two stacked pillows that extend across the stomach cavity;

FIG. 8 is a perspective view of the device of FIG. 7, and FIG. 8A is a cross-section through a flow-through esophageal sphincter tube thereof;

FIGS. 14-16A illustrate components of the device of FIG. 11; and

DETAILED DESCRIPTION OF THE PREFERRED EMBODIMENTS

The present invention is directed to a variety of different intragastric devices that passively treat obesity by taking up space within the stomach or contacting areas in and around the stomach to induce feelings of satiety. Furthermore, some devices described herein affect the rate of stomach intake. It should be understood that a number of the disclosed devices provide more than one of these passive aspects, and also that any disclosed structure could be combined with another disclosed structure unless physically impossible. As such, combinations of the passive satiety-inducing features disclosed herein, even if not explicitly stated, are contemplated. The term "passive" refers primarily to a lack of any moving parts within the devices, but in general to the inert nature of the various devices. A passive device as defined herein, however, is not one that cannot affect change or stimulate the stomach, but rather one that may do so without any physical or chemical changes to its basic makeup.

Figure 1:
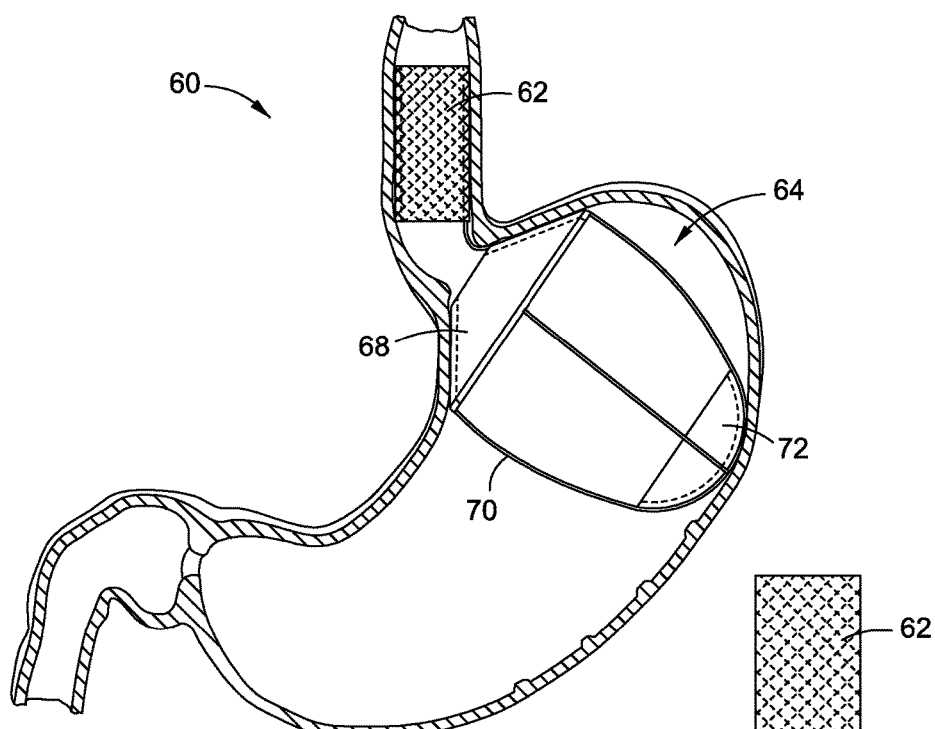
FIG. 1 illustrates a still further intragastric obesity treatment device in the stomach having an esophageal stent tethered to a cardia-stimulating member.

FIG. 1 illustrates a first intragastric device 60, but also illustrates the anatomy of the human stomach, which will be described first. The major function of the stomach is to temporarily store food and release it slowly into the duodenum. The esophagus extending downward from the mouth connects to the stomach via esophageal sphincter, which regulates flow food into the stomach cavity. The cardia surrounds the superior opening of the stomach. The rounded portion superior to the body and adjacent the cardia is the fundus. Inferior to the fundus is the large central portion of the stomach, called the body that is lined with muscles that contract and relax repetitively to churn the food therein. The stomach processes the food to a semi-solid "chyme," which enables better contact with the mucous membrane of the intestines, thereby facilitating absorption of nutrients. In addition, the stomach is an important site of enzyme production.

Lower down in the stomach the antrum connects the body to the pylorus, which leads into the duodenum. Below the stomach, the duodenum leads into the upper part of the small intestine (not shown); the jejunum makes up about one-third of the small intestine. The region of the stomach that connects to the duodenum is the pylorus. The pylorus communicates with the duodenum of the small intestine via the pyloric sphincter (valve). This valve regulates the passage of chyme from stomach to duodenum and it prevents backflow of chyme from duodenum to stomach.

Figure 2:
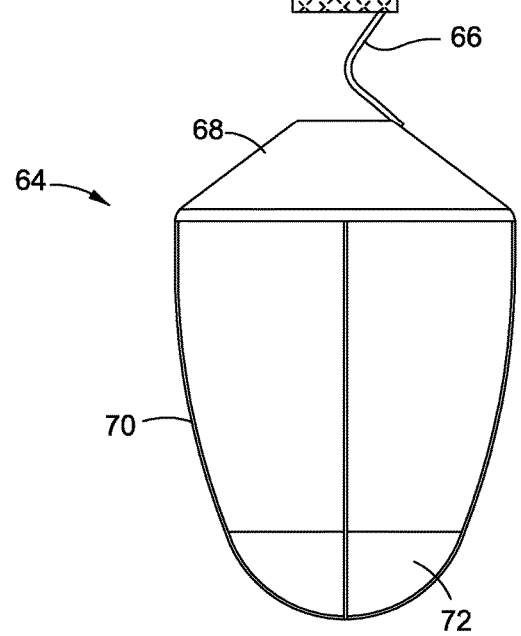
FIG. 2 is an elevational view of the device.

The intragastric device 60 shown in FIGS. 1 and 2 applies pressure to the cardia and includes an esophageal stent 62 with a cardia-stimulating bowl 64 attached thereto. The esophageal stent 62 is adapted to be placed in the lower portion of the esophagus, just above the esophageal sphincter. The esophageal stent 62 helps prevent device migration over time. The stent 62 attaches to a thin flexible tether 66, that in turn attaches to a flexible, flat partial conical ring 68 made of thin material. The tether 66 is attached and configured so it passes thought the center of the esophageal sphincter, and thus, in conjunction with its small profile, permits complete closure of the sphincter without obstructing sphincter action. This geometry is intended to reduce the chance for acid reflux due to stressing of the sphincter by off-center pulling/favoring one side or another.

Wire-like anchor legs 70 attach to and push up against the conical ring 68. The legs 70 are made of a springy material and slightly folded, with a pre-load spring force, which pushes the conical ring 68 upward against the cardia walls of the stomach. The conical ring 68 includes a central through hole centered at the esophageal sphincter through which food passes. The legs 70 mount at their opposite ends, to a wide, thin cup 72, which is shallow like the upper conical ring 68. The purpose of the cup 72 is to cushion the legs 70 against the greater curvature of the stomach, where it rests/presses. The shallow cup 72 is sized to create large spaces between itself and the conical ring 68, and between the legs 70, so that food may easily pass therethrough. There are preferably at least four legs 70 as shown for even compression of the conical ring 68 against the cardia, though more than four may be used.

For device insertion and removal, a lubricated, Teflon or similar material, thin-walled tube (not shown) would be inserted down the esophagus, and partially into the stomach, with the device 60 compressed and pre-loaded inside the tube. Then the device would be maintained in its location by using a foot-ended wire or similar obturator, to bear on the compressed mass, and the tube would be pulled back up the esophagus, and extracted through the mouth, leaving the device in place. While the tube is removed, the device would "spring open" to its original/non-compressed shape.

Figure 5:
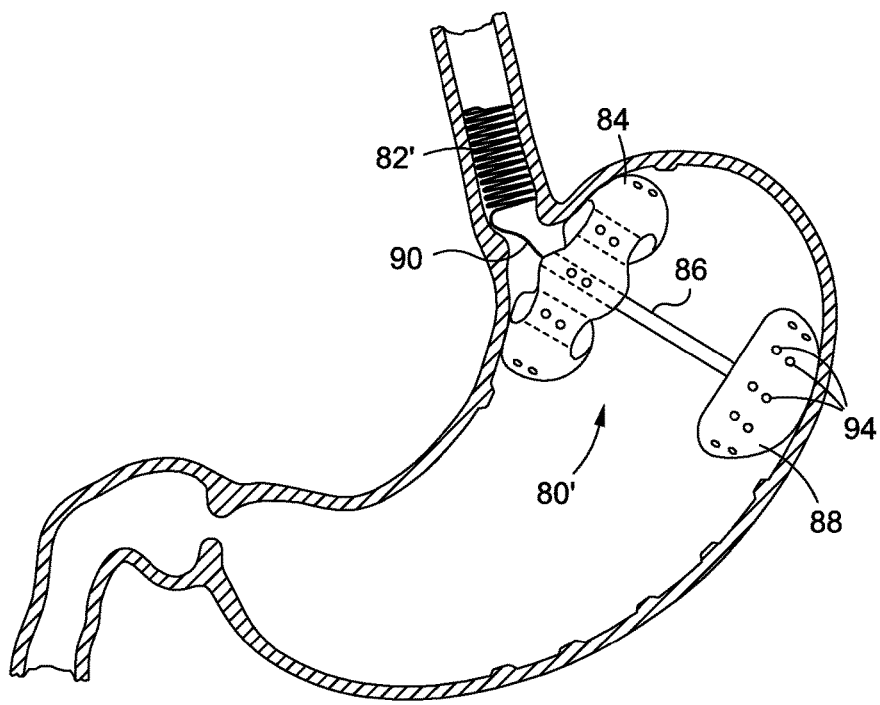
FIG. 5 shows an alternative obesity treatment device having a cardia-stimulating pillow.
Figure 6:
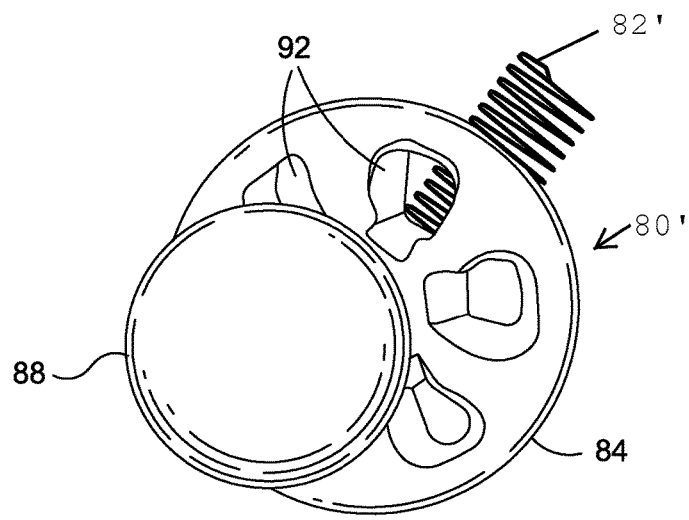

An alternative cardia-stimulating device 80 shown in FIGS. 3 and 4 comprises a tubular esophageal stent 82 tethered to a cardia-stimulating pillow 84. The cardia-stimulating pillow 84 is a compliant balloon-like structure held in place just below the esophageal sphincter. A thin, relatively stiff tube 86 connects the pillow 84 to a smaller compliant, balloon-like pillow 88. An alternative device 80' shown in FIGS. 4A, 5 and 6 features the same structures except the esophageal stent 82' is formed as a coil, such as Nitinol, as opposed to a conventional tubular lattice. Esophageal deployment and removal of the device is achieved by the ability of the stent 82 to collapse, and the ability of the pillows 84 and 88 to fold around the small diameter center tube 86. A tether 90 mounts to the stent and is shaped so that it runs through the center of the sphincter opening. The small profile of the tether 90 eliminates any uneven pressure on the circumferential walls of the sphincter.

The cardia-stimulating pillow 84 has a central opening that aligns with the esophageal sphincter to permit food to pass therethrough. In the illustrated embodiment, the cardia-stimulating pillow 84 comprises a substantially disk-shaped member having large spoke-like through holes for passage of food. Specifically, a series of spoke-like through holes 92 in the pillow 84 open to a top-facing central recess or concavity above a hub member 91 and provide a passageway for food passing down the esophagus into the stomach. There are 6 spoke-like holes 92 as shown, though more or less could be used. The hub member 91 connects to inward extensions 93 of the pillow 84 and to both the tube 86 and tether 90, thus providing a central structural support for these elements. Both the top and bottom surfaces of the pillow 84 are scalloped, as best seen in FIG. 3, which helps channel food through the holes 92.

Both the pillows 84 and 88 are hollow balloon-like structures that take up volume in the stomach and are intended to cushion the device ends against the stomach walls, helping to prevent ulceration. These uninflated "balloons" are molded with relatively thick walls, so they maintain their as-molded shape without inflation. Holes 94 in the sides of the pillows 84 and 88 allow stomach juices to freely flow in and out. Furthermore, a series of holes are provided in the tube 86 to permit free flow of stomach juices.

While consuming a meal, the stomach is known to produce peristaltic convolutions throughout. As such movement occurs, the device 80 is squeezed, thereby applying intermittent pressure to the cardia area of the stomach. That is, contraction of the stomach walls reduces the distance across the stomach walls and necessarily places the stiff tube 86 in compression, which pushes the cardia-stimulating pillow 84 against the cardia. Such pressure is known to stimulate the release of satiety-inducing hormones, thus reducing meal time and food intake.

Another cardia-stimulating device 100 is shown in FIGS. 7 and 8 that includes a single use GI implant whereby two, stacked, compliant "pillow"-like structures support a single, thinner-walled balloon that acts as an artificial stomach pouch, similar to the pouch created by an externally-placed gastric band. More particularly, the cardia-stimulating device 100 comprises an esophageal anchoring stent 102 attached via a compliant, collapsible tube 103 through the esophageal sphincter to an artificial stomach pouch 104. Two stacked hollow pillows 106, 108 the hold stomach pouch 104 against the cardia end area surrounding the esophageal sphincter. The stomach pouch 104 and pillows 106, 108 are molded with relatively thick walls, so they maintain their as-molded shape without inflation.

The outer pillow 108 bears against the Greater Curvature of the stomach and sandwiches the middle pillow 106 against the stomach pouch 104. Holes 110 in the pillows 106, 108 permit stomach juices to flow freely through. In the illustrated embodiment, the balloon-like pillows 106, 108 each have a substantially hemispherical shape and are arranged so that their equatorial planes abut and their spherical surfaces face away from one another. This helps absorb forces from the stomach wall and transfer them to the stomach pouch 104.

A tubular leg 112, extending from the outer pillow 108 serves as an anti-rotational feature, to help keep the esophageal tube 103 from twisting, and therefore obstructing flow-through of food. That is, the tubular leg 112 tends to maintain the orientation shown, pointing down the relatively shallow sloping length of the stomach, rather than rotating up to areas of greater curvature.

The cross-section of the esophageal tube 103 is seen in FIG. 8A and includes a series of longitudinal folds that create a highly collapsible structure. The sphincter is believed to be able to close over the compliant esophageal tube 103 in a nearly normal, fully sealing fashion. The tube 103 thereby provides a leak-proof passageway for food from the esophagus, to enter directly into the balloon/artificial stomach.

A stoma opening 114 in the stomach pouch 104 allows emptying of food into the biological stomach for normal digestion to occur. As food accumulates in the artificial stomach pouch 104, it fills and applies pressure to the cardia. Such pressure is known to trigger release of satiety-inducing hormones, so eating will taper and cease prematurely. Since a smaller than normal quantity of food has been ingested, weight loss could occur. This cardial pressure from nearby retained food is (currently) thought to be the primary mechanism that allows external gastric bands to function as it does. Additionally, the rate at which the entire stomach fills is slowed by the artificial stomach pouch 104.

Figure 9:
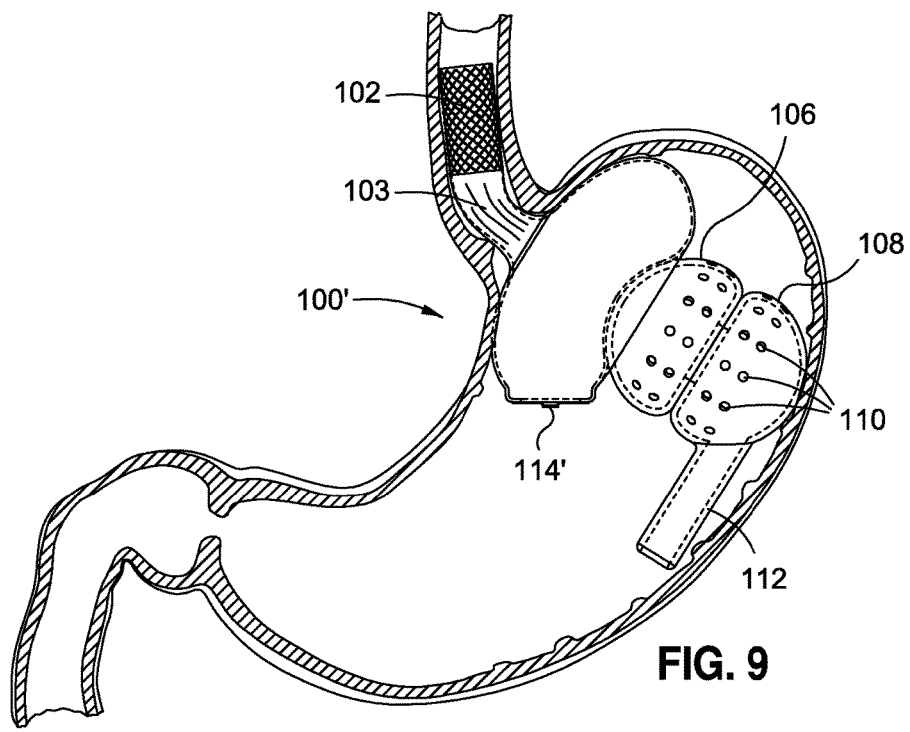
FIG. 9 shows an obesity treatment device similar to that in FIG. 7.
Figure 10:
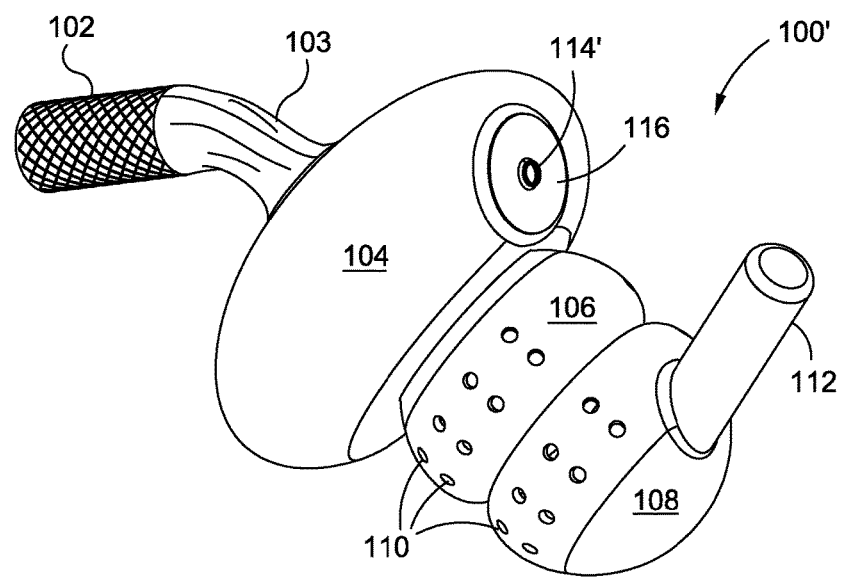
FIG. 10 is a perspective view thereof.
Figure 11:
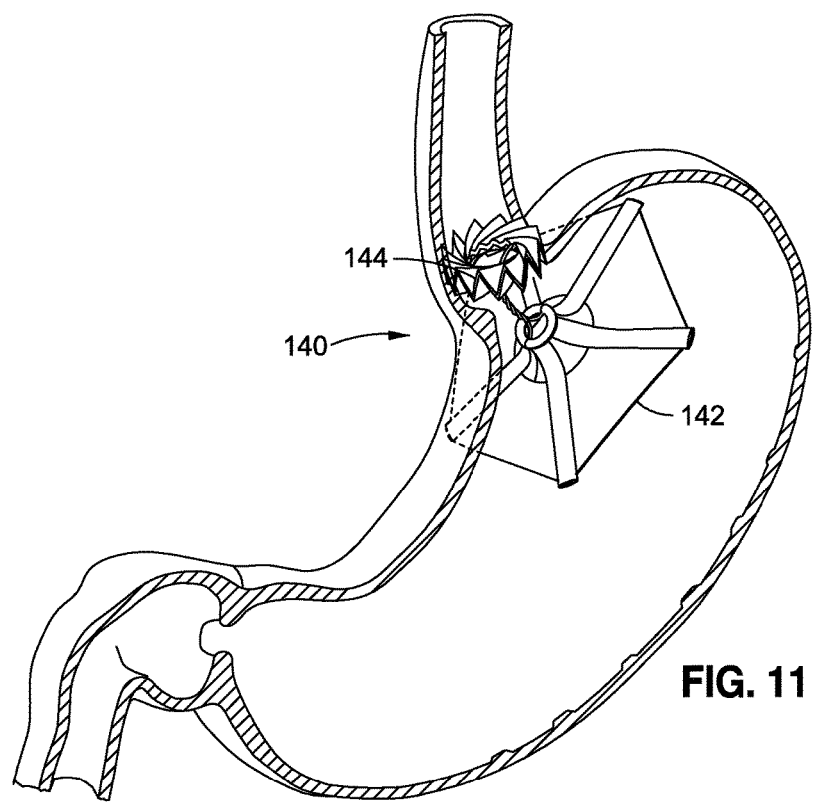
FIG. 11 illustrates a still further cardia-stimulating intragastric obesity treatment device having a constant aperture expandable anchoring member.

An alternative version of the cardia-stimulating device 100' is shown in FIGS. 9 and 10 and has almost the same features as described above with a slightly different stoma opening 114'. Instead of a constant diameter passage, as in FIGS. 7 and 8, the stoma opening 114' is defined in the center of a thin-walled diaphragm 116 bonded to a larger opening on the artificial stomach pouch 104. The diaphragm 116 stretches as the stomach pouch 104 fills with food, and eventually permits egress of the food into the larger natural stomach cavity. In contrast to the relatively inflexible stoma opening 114 above, this flexible stoma 114' accommodates a somewhat larger sudden influx of food, and the opening 114' itself stretches to permit larger amounts to pass through.

Esophageal deployment of the device 100 can be achieved by the pre-assembled components' ability to collapse and fit comfortably into a Teflon or similar low friction tube. The device 100 may come pre-loaded in this configuration. The pre-loaded delivery tube is fed down the esophagus where the stent 102 is permitted to expand. Then the lower portion of the device is deployed into the stomach. For device removal, an empty tube is fed down the esophagus, as far down as the stent. Next, a standard grabber can be inserted down the tube and the entire device can be grabbed and pulled into the tube. Then the tube is removed with the device re-loaded inside.

A still further device 140 designed to stimulate the cardia and induce feelings of satiety is seen in FIGS. 11-16. The device 140 comprises a gastro-esophageal umbrella 142 that is implanted transorally, across the gastro-esophageal (G-E) junction, during a minimally invasive gastroendoscopic surgical procedure. The device 140 is held in place within the esophagus with a mounting stent 144. The umbrella 142, connected to the mounting stent 144 with a tether 146, is situated within the stomach compartment and exerts local pressure on the cardia of the stomach in order to create a sense of fullness. At the conclusion of treatment, the device is retrieved gastroendoscopically.

Figure 13A:
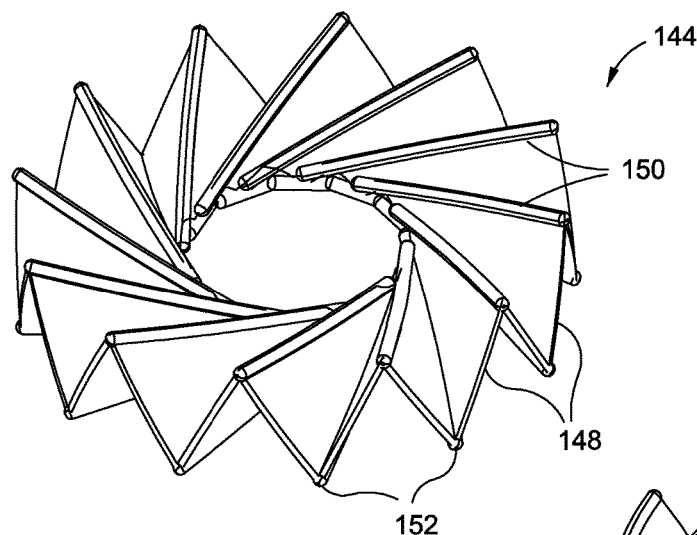
FIGS. 13A-13D are perspective views of the expandable anchoring member of the device of FIG. 11 in varying expanded states.
Figure 13B:
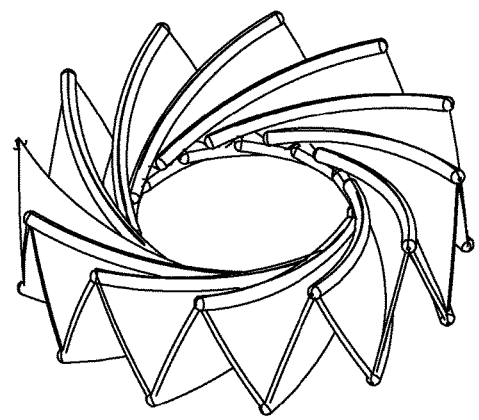
Figure 13C:
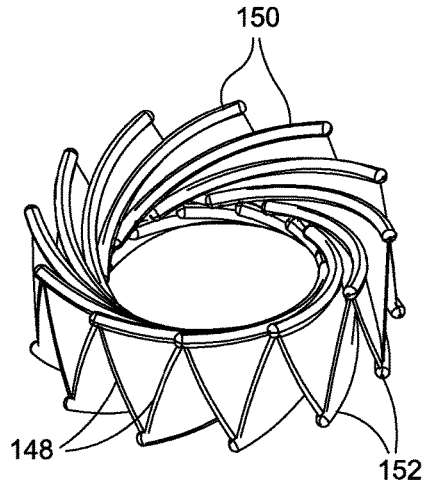
Figure 13D:
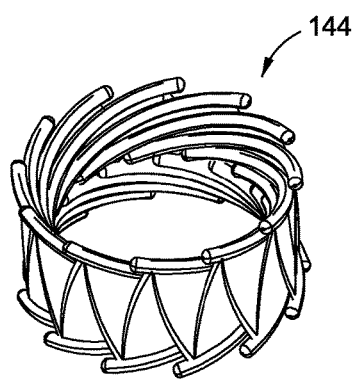

The esophageal mounting stent 144 must not interfere with the normal function of the esophagus and must provide sufficient holding capability (no migration within esophagus). The stent 144 has geometry as seen in FIGS. 13A-13D that allows it to, under small changes in radial force, dramatically change its outer diameter while maintaining its inner diameter. To do this, an accordion-like spiral structure include a plurality of triangular membranes 148 that are each bordered on two sides by an upper strut 150 and a lower strut 152, with the outer edge being free. FIG. 13A shows this geometry the clearest, with the membranes 148 alternating at angles to one another to form a zigzag pattern around the stent 144. The membranes 148 are highly flexible as are the struts 150, 152, so that the accordion-like arrangement can flex open as in FIG. 13A and then constrict as in FIG. 13D. The struts 150, 152 are slightly arcuate and cooperate to maintain a minimum inner diameter of the stent 144, as seen in FIG. 13D.

Therefore, the stent 144 is designed to accommodate the reduction in esophageal diameter that occurs during peristalsis while still maintaining an unobstructed pathway for a bolus to pass. It is believed that by offering minimal resistance to the natural peristaltic contractions of the esophagus, the device is less likely to migrate. Added resistance to migration can be achieved by assembling multiple esophageal mounting components in series with one another, all connected to the tether 146. The stent 144 may be assembled from a metal mesh similar to existing esophageal stents in order to give the component sufficient structural rigidity. The orientation and design of the mesh needs to be one such that the deformation shown in FIGS. 13A-13D is still achievable. The esophageal mounting component may be made from materials including (but not limited to) rubbers, fluorosilicones, fluoroelastomers, thermoplastic elastomers, thermoplastics, thermosets, metals, glass, or any combinations thereof.

The tether 146 seen in FIG. 14 connects the esophageal mounting stent 144 to the gastro-esophageal umbrella 142. In this embodiment, the tether 146 comprises a braided wire, which may be elastic or more rigid in the longitudinal direction. An elastic wire is less sensitive than a rigid wire as far as the placement of the esophageal mounting component within the esophagus. This is because the umbrella 142 must be exerting pressure on the stomach walls, which may not happen if the esophageal mounting component is not placed carefully. An elastic tether 146 allows the surgeon a wider range of placements within the esophagus while still maintaining pressure on the stomach walls. The tether 146 should be of a minimal diameter and attach itself to the other two components in such a way that its presence across the G-E junction does not interfere with the function of the G-E sphincter. The tether may be made from materials including (but not limited to) rubbers, fluorosilicones, fluoroelastomers, thermoplastic elastomers, thermoplastics, thermosets, metals, or any combinations thereof.

Figure 12:
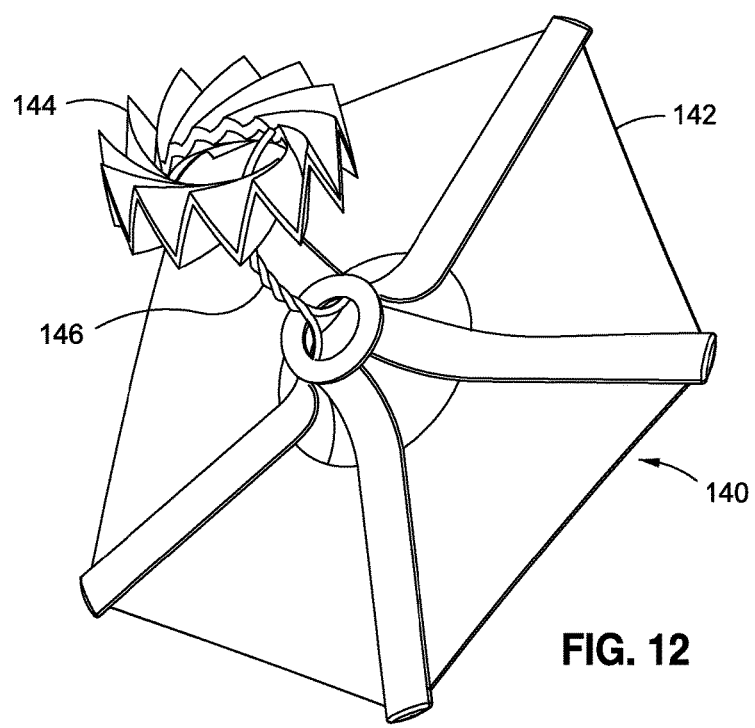
FIG. 12 is a perspective view thereof.

The gastro-esophageal umbrella 142 exerts pressure on the stomach walls. The umbrella 142 comprises a plurality of struts or strips 156 splayed outward from a lead-in hub 154, and flexible webbing 158 extending between the strips 156. The natural or relaxed shape of the umbrella 142 is splayed open, as seen in FIGS. 12 and 15, although it can be deformed into a more columnar shape as seen in FIGS. 16 and 16A for implantation/explantation. The umbrella 142 desirably has at least five strips 156 which are fairly stiff structures (although elastic enough to allow for deformation to the columnar delivery shape) compared to the webbing 158. The webbing 158 is a thinner material, which allows for a more complete circumferential contact area with the stomach. The central hub 154 is an open ring for food to pass such that this device does not inhibit the normal passage of food. The G-E umbrella 142 may be made from materials including (but not limited to) rubbers, fluorosilicones, fluoroelastomers, thermoplastic elastomers, thermoplastics, thermosets, metals, or any combinations thereof.

While not shown, the outer surface of the intragastric implants disclosed herein may further include additional uneven surface features such as small rounded bumps or protrusions, quill-like extensions, dimples or recesses, and the like. These features, upon contact with the inner stomach wall of the patient may further trigger hormone release or otherwise aid the patient in feeling full. Such features may be particularly effective for those embodiments which stimulate the cardia. The examples in FIGS. 17-19 may be applied to any of the various implants and surfaces disclosed herein.

Figure 17:
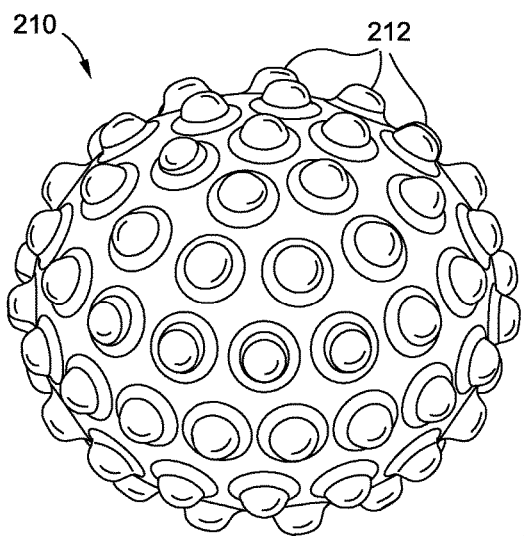
FIGS. 17-19 illustrate intragastric implant surface features that provide additional stomach cavity stimulation.

For instance, FIG. 17 illustrates a spherical intragastric implant 210 having numerous external protrusions or bumps 212 projecting outward therefrom. These bumps 212 separately contact the inner walls of the stomach, potentially increasing the stimulation to the surrounding satiety-sensing nerves. As shown, a plurality of bumps 212 may be equally spaced apart on the outer surface and interspersed with flat portions. In one embodiment, the bumps 212 may be of equal heights and diameters, or they may be configured to have different heights and/or diameters. For example, having bumps 212 with different heights and/or diameters may be advantageous for preventing the stomach from adjusting to the bumps. The bumps 212 separately contact the inner walls of the stomach, potentially increasing the stimulation to the surrounding satiety-sensing nerves.

Figure 18:
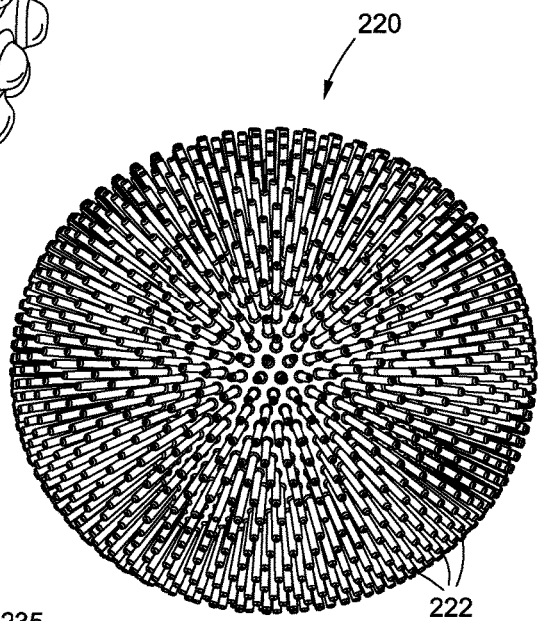

Another example of exterior stimulation features is seen in FIG. 18, where an intragastric implant 220 formed as a sphere features a multitude of small flagella or quill-like extensions 222 extending outward therefrom. As shown, a plurality of extensions 222 may be equally spaced apart. In one embodiment, the extensions 222 may be of equal heights and diameters, or they may be configured to have different heights and/or diameters. In one embodiment, the extensions 222 may be extremely flexible and may bend when a pressure is exerted on them from the inner stomach wall of the patient. Alternatively, the extensions 222 may be stiffer and might not bend as much when a pressure is exerted on them from the inner stomach wall of the patient. In another embodiment, some of the extensions 222 may have a first flexibility while some of the extensions may have a second flexibility.

Figure 19:
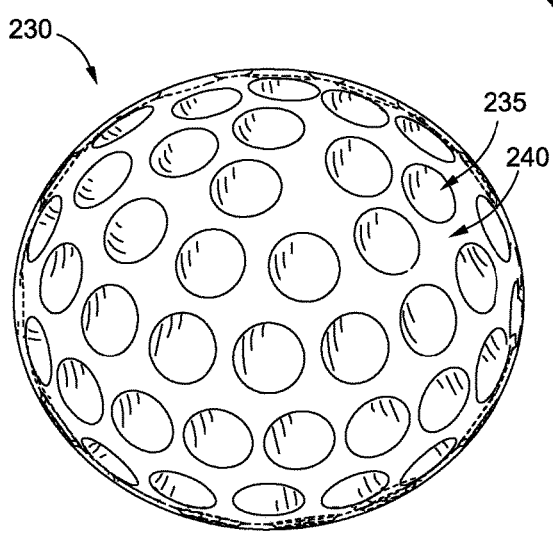

FIG. 19 illustrates another example of uneven surface features on an intragastric implant 230. As shown, the intragastric implant 230 is a substantially spherical object with recesses or dimples 235 extending inward from the surface of the intragastric implant 230. In one embodiment, the intragastric implant 230 may be considered to have a surface comprised of recesses 235 and flat portions 240. As shown, a plurality of recesses 235 may be equally spaced apart on the outer surface. As shown, recesses 235 do not contact each other, and may be of equal heights and diameters. In addition to being depressed, the recesses 235 may employ a thinner wall. For example, if the flat portions 240 have a wall thickness of 20 millimeters, the recesses 235 may have a wall thickness of 10 millimeters. With a thinner wall, the recesses 235 may be more susceptible to larger strains. The intragastric implant 230 is effectively triggered in the patient's stomach by stomach contractions. These stomach contractions increase the pressure in the intragastric implant 230. If one recess 235 is not in contact with the stomach wall, it will deform outward until it comes into contact with the stomach wall.

It should be noted that the bumps 212, quill-like extensions 222, or recesses 235 shown in FIGS. 17-19 may be provided in a non-uniform distribution. That is, a regular array of such exterior features may stimulate the stomach wall more than a smooth surface, but also providing a non-uniform distribution will create different sensations on a constantly changing basis.

It should also be stated that any of the embodiments described herein may utilize materials that improve the efficacy of the device. For example, a number of elastomeric materials may be used including, but not limited to, rubbers, fluorosilicones, fluoroelastomers, thermoplastic elastomers, or any combinations thereof. The materials are desirably selected so as to increase the durability of the device and facilitate implantation of at least six months, and preferably more than 1 year.

Material selection may also improve the safety of the device. Some of the materials suggested herein, for example, may allow for a thinner wall thickness and have a lower coefficient of friction than the current device which may aid in the natural passage of the balloon through the GI tract should the device spontaneously deflate.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:
  a. Silicone materials used include 3206 silicone for any shells, inflatable structures, or otherwise flexible hollow structures. Any fill valves will be made from 4850 silicone with 6% $BaSo_4$. Tubular structures or other flexible conduits will be made from silicone rubber as defined by the Food and Drug Administration (FDA) in the Code of Federal Regulations (CFR) Title 21 Section 177.2600.

Purposes:
  i. the devices are for human implant,
  ii. the devices are intended to occupy gastric space while also applying intermittent pressure to various and continually changing areas of the stomach;
  iii. the devices are intended to stimulate feelings of satiety, thereby functioning as a treatment for obesity.

General Implant Procedures:
i. The device is intended to be implanted transorally via endoscope into the corpus of the stomach.
ii. Implantation of the medical devices will occur via endoscopy.
iii. Nasal/Respiratory administration of oxygen and isoflurane to be used during surgical procedures to maintain anesthesia as necessary.

One exemplary implant procedure is listed below.
i. Perform preliminary endoscopy on the patient to examine the GI tract and determine if there are any anatomical anomalies which may affect the procedure and/or outcome of the study.
ii. Insert and introducer into the over-tube.
iii. Insert a gastroscope through the introducer inlet until the flexible portion of the gastroscope is fully exited the distal end of the introducer.
iv. Leading under endoscopic vision, gently navigate the gastroscope, followed by the introducer/over-tube, into the stomach.
v. Remove gastroscope and introducer while keeping the over-tube in place.
vi. OPTIONAL: Place the insufflation cap on the over-tubes inlet, insert the gastroscope, and navigate back to the stomach cavity.
vii. OPTIONAL: Insufflate the stomach with air/inert gas to provide greater endoscopic visual working volume.
viii. Collapse the gastric implant and insert the lubricated implant into the over-tube, with inflation catheter following if required.
ix. Under endoscopic vision, push the gastric implant down the over-tube with gastroscope until visual confirmation of deployment of the device into the stomach can be determined.
x. Remove the guide-wire from the inflation catheter is used.
xi. If inflated: Inflate the implant using a standard Bio-Enterics Intragastric Balloon System ("BIB System") Fill kit.
xii. Using 50-60 cc increments, inflate the volume to the desired fill volume.
xiii. Remove the inflation catheter via over-tube.
xiv. Inspect the gastric implant under endoscopic vision for valve leakage, and any other potential anomalies. Record all observations.
xv. Remove the gastroscope from over-tube.
xvi. Remove the over-tube from the patient.

End Point Criteria:
Weight Loss
Comprehensive Metabolic Panel (CMP)
HbA1C
Lipid Panel
Tissue Samples/Response Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A passive intragastric obesity treatment implant, comprising:
   an esophageal stent sized to anchor within the esophagus just above the esophageal sphincter;
   a shallow conical ring sized to contact the interior stomach walls adjacent to the esophageal sphincter with a central through hole centered at the esophageal sphincter;
   a thin, flexible tether connecting the esophageal stent to the conical ring;
   a plurality of thin anchor legs extending from a distal rim of the conical ring, the legs made of a resilient material and sized and oriented to extend from the cardia to an interior stomach wall opposite the esophageal sphincter in an implanted configuration; and
   a shallow cup member attached to the anchor legs opposite from the conical ring such that the conical ring and shallow cup are spaced apart from each other to provide a passage for food therebetween,
   the implant being formed of materials that permit it to be compressed into a substantially linear transoral delivery configuration and that will resist degradation over a period of at least six months within the stomach.

2. The implant of claim 1, wherein there are four anchor legs.

3. The implant of claim 1, wherein the tether is flexible while the anchor legs are relatively stiffer than the tether and sufficiently stiff to transmit compressive forces from the cup member to the conical ring.

4. A passive intragastric obesity treatment implant, comprising:
   an esophageal stent sized to anchor within the esophagus just above the esophageal sphincter;
   a cardia-stimulating pillow having perforations, and at least one opening adjacent the esophageal sphincter to permit food to pass therethrough and into the stomach;
   a flexible tether securing cardia-stimulating pillow to the esophageal stent;
   a balloon-like pillow smaller than the cardia-stimulating pillow having perforations therein; and
   a thin tube connecting the cardia-stimulating pillow and the balloon-like pillow, the tube relatively stiffer than the pillows and having a length sufficient to maintain contact of the cardia-stimulating pillow against the cardia and the balloon-like pillow against the stomach wall opposite the esophageal sphincter,
   the implant being formed of materials that permit it to be compressed into a substantially linear transoral delivery configuration and that will resist degradation over a period of at least six months within the stomach.

5. The implant of claim 4, wherein the cardia-stimulating pillow comprises a substantially disk-shaped member having large spoke-like through holes for passage of food.

6. The implant of claim 4, wherein the cardia-stimulating pillow further includes a central hub connected to both the tube and tether.

7. The implant of claim 4, wherein the esophageal stent comprises a coil of elastic material.

8. The implant of claim 7, wherein the coil material is Nitinol.

9. The implant of claim 4, wherein the cardia-stimulating pillow and the balloon-like pillow are molded with walls of sufficient thickness to maintain their as-molded shape without inflation, and each includes holes to allow stomach juices to freely flow in and out.

10. A passive intragastric obesity treatment implant, comprising:
    a tubular element sized for placement at least partly in the esophagus, the tubular element including an esophageal stent and a flexible tubular connector, the esophageal stent being sized to anchor within the esophagus just above the esophageal sphincter;
    an enlarged cardia-stimulating pillow coupled to the flexible tubular connector to abut the esophageal opening and being open to the esophagus, the pillow including an artificial stoma opening to the stomach cavity, wherein the tubular element permits food to flow therethrough to the pillow; and
    a plurality of balloon-like pillows having perforations stacked against the cardia-stimulating pillow so as to reach the interior stomach wall opposite the esophageal sphincter and thus maintain contact of the cardia-stimulating pillow against the cardia; and
    the implant being formed of materials that permit it to be compressed into a substantially linear transoral delivery configuration and that will resist degradation over a period of at least six months within the stomach.

11. The implant of claim 10, wherein the artificial stoma comprises an aperture in a flexible diaphragm such that the artificial stoma has a variable diameter.

12. The implant of claim 10, further comprising an anti-rotation leg attached to an outer one of the balloon-like pillows.

13. The implant of claim 10, wherein there are two balloon-like pillows each having a substantially hemispherical shape and arranged so that their equatorial planes abut.

14. The implant of claim 10, wherein the balloon-like pillows are molded with walls of sufficient thickness to maintain their as-molded shape without inflation, and each includes holes to allow stomach juices to freely flow in and out.

15. The implant of claim 10, wherein the flexible tubular connector is collapsible, and wherein the cardia-stimulating pillow is tethered to the esophageal stent by the collapsible tubular connector between the esophageal stent and the cardia stimulating pillow.

* * * * *